United States Patent [19]

O'Lenick, Jr.

[11] Patent Number: 5,034,555

[45] Date of Patent: Jul. 23, 1991

[54] NOVEL ALKOXYLATED AMIDO SULFATES

[75] Inventor: Anthony J. O'Lenick, Jr., Lilburn, Ga.

[73] Assignee: LCE Partnership, Lake Geneva, Wis.

[21] Appl. No.: 379,284

[22] Filed: Jul. 13, 1989

[51] Int. Cl.$^5$ .................................. C07C 141/00
[52] U.S. Cl. ................................................ 558/30
[58] Field of Search ........................................ 558/30

[56] References Cited

U.S. PATENT DOCUMENTS 1,932,180 10/1933 Guenther et al. .................. 558/30

Primary Examiner—Nicky Chan

[57] ABSTRACT

The present invention deals with the composition, and application of novel alkoxylated amido sulfates, useful as surface active agents. Compounds of this invention have foaming, emulsification, wetting, softening, anti-tangle, and conditioning properties. The compounds of the current invention conform to the following structure;

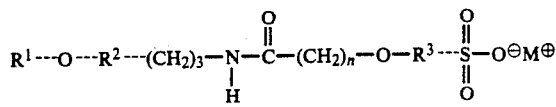

$R^1$ is alkyl having from 6 to 40 carbon atoms;

$R^2$ is $-(CH_2-CH_2-O)_x-(CH_2-CH-O)_y-(CH_2-CH_2-O)_z-$;

$R^3$ is $-(CH_2-CH_2-O)_a-(CH_2-CH-O)_b-(CH_2-CH_2-O)_c-$;

n is an integer from 1 to 10;

x, y and z are independently integers from 0 to 20;

a, b and c are independently integers from 0 to 20;

M is an selected from Na, K, Li, Ba, Mg, Ca, NH4, and is needed for charge balance.

13 Claims, No Drawings

ALKOXYLATED AMIDO SULFATES

BACKGROUND OF THE INVENTION

1. Field of the Invention

The present invention deals with the composition, and application of novel alkoxylated amido sulfates, useful as surface active agents. Compounds of this invention have foaming, emulsification, wetting, softening, anti-tangle, and conditioning properties. They also exhibit an ability to emulsify larger quantities of oil and other hydrophobic materials than standard emulsifiers.

2. Description of the Art Practices

The nature and structure of the amido group in the molecules of the present invention are of major significance to the novel functional attributes of the compounds of the invention. This novel structure comes from the synthetic route used to make the novel alkanolamides. Traditional alkanolamides have been known for many years and have been widely used in many market segments as foam boosters, emulsifiers, antistats and corrosion inhibitors. Chemically, these alkanolamides are the reaction product of an alkanolamine and a fatty material. Fatty materials are a class of compounds which include fatty carboxylic acids, fatty methyl esters and fatty glycerides (also called oils). The source of the fatty materials include coconut, peanut, soybean, and rapeseed oils, fractionated and non-fractionated fatty methyl esters and acids of almost any carbon length.

U.S. Pat. No. 2,089,212 to Kritchevsky issued August 1937, details the production of fatty alkanolamides from ethanolamines and fatty acids. U.S. Pat. No. 2,094,609, to Mead details the development of the conventional alkanolamide process to make products derived from fatty esters and glycerides.

Despite their wide use and commercial acceptance, alkanolamides have had some short comings. They are generally used in combination with a foaming agent like sodium lauryl sulfate to provide foam stabilization. There are significant practical limitations in the range of applicability of these materials as truly multi-functional surface active agents. The reason for this is that the variables which can be altered in traditional alkanolamide chemistry is limited to the choice of fatty material and the choice of alkanolamine. This molecular limitation results in limitations on properties obtainable in alkanolamides (for example, alkanolamides are seldom used as primary foamers).

In addition traditional alkanolamides have come under suspicion for containing nitrosamines, which are potent cancer causing agents. The nitrosamine is formed by an undesirable side reaction of the alkanolamine. There have been recent efforts by industry to keep the free alkanolamine level present in alkanolamides as low as possible to minimize the concentration of nitrosamines. This approach has met with limited success since the alkanolamide is in equilibrium with several reactive species. Consequently, the preparation of an alkanolamine free alkanolamide using conventional amide technology is highly questionable.

Fatty alcohol sulfates and more recently fatty alcohol ether sulfates have been known for many years and are the workhorse of the personal care industry. While the former is an excellent detergent, the latter class of materials have become a factor in recent years because of the consumer's desire for low irritation personal care products. Selection of the correct sulfate is another complication. With any given molecule, there is a trade off between detergency and lower irritation. Higher molecular weight alcohols generally give less irritating sulfates, however the higher molecular weight species are generally solid. Sulfation of solid alcohols (i.e. those linear compounds with more than 16 carbons) represents several technical and production problems. The higher temperatures of sulfation and paste nature of the finished products represents a major draw back. One other option to get less irritating sulfates is to add ethylene oxide. Sodium laureth 5 mole ethoxylate sulfate is much less irritating than sodium lauryl sulfate, however the added ethylene oxide makes it more water soluble and consequently it is not a good detergent. Lastly, incorporation of an amido function into a surface active molecule is a commonly used method to lower irritation. Cocobetaine is much more irritating than cocamidopropylbetaine. Alkanolamide based ether sulfates are known and enjoy some sales, although their popularity when compared to ether sulfates is quite low. This type of material are typically based upon the reaction of a cocomonoethanolamide or an ethoxylated coco- monoalkanol amide with a suitable sulfating agent using procedures known to those skilled in the art. The products of this reaction are good lime soap dispersants and show some additional surface active properties. A major problem encountered with the sulfated ethanolamides is hydrolysis. The sulfate group is positioned in such a way that the hydrolysis occurs by an energetically favored 6 member ring transition molecule. Compounds of the present invention have the nitrogen and carboxyl group in the compound reversed so that there is no six member transition state possible. As will become apparent later this results in significantly improved alkaline stability.

U.S. Pat. No. 3,5622,170 issued in 1971 to Zorayam teaches that some of the hydrolytic instability can be overcome by using a diglycolamine based alkanolamide in synthesis of a sulfate. While this advance gives some increased stability, it is not as effective as the reversal of the position of the carboxyl (C=O) function and the amine group (NH) disclosed by this invention.

STANDARD PRODUCT

Reaction of Fatty Acid with Alkanolamine

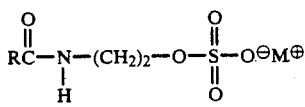

ZORAYAM PRODUCT

Reaction of Fatty Acid with Alkanolamine

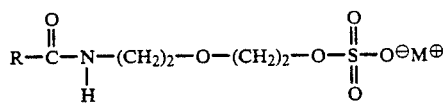

COMPOUNDS OF THIS INVENTION

Reaction of Fatty Amine with Lactone

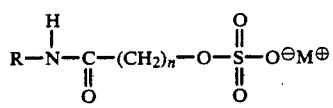

OBJECT OF THE INVENTION

One aspect of the invention relates to a new class of intermediates which are multi-functional alkanolamides which are not based upon alkanolamines. These products are based upon the reaction of an alkoxylated fatty primary ether amine with a lactone under mild temperatures to give alkoxylated ether amide. The resulting novel alkanolamide is sulfated using processes known to those skilled in the art.

An additional aspect of the invention is the fact that the sulfated derivatives of these materials because they are not based upon alkanolamines, do not contain nitrosamines.

An additional aspect of this invention is the finding that stable microemulsions can be prepared using the compounds of this invention.

Still another aspect of the invention relates to the incorporation of a regiospecific beta branched ether amine based upon guerbet alcohols into the alkanolamide. As will become apparent, the liquidity and high molecular weight of the guerbet moiety, makes these products well suited for applications like personal care were low irritation and substantivity is important. The branched hydrophobe also makes the final surfactant a better oil emulsifier than linear products.

THE INVENTION

The compounds of the current invention conform to the following structure;

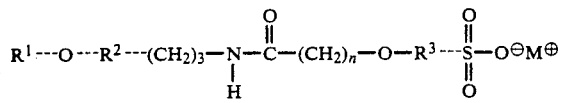

$R^1$ is alkyl having from 6 to 40 carbon atoms;
$R^2$ is $-(CH_2-CH_2-O)_x-(CH_2-CH(CH_3)-O)_y-(CH_2-CH_2-O)_z-$;
$R^3$ is $-(CH_2-CH_2-O)_a-(CH_2-CH(CH_3)-O)_b-(CH_2-CH_2-O)_c-$;
n is an integer from 1 to 10;
x, y and z are independently integers from 0 to 20;
a, b and c are independently integers from 0 to 20;
M is an selected from Na, K, Li, Ba, Mg, Ca, NH4, and is needed for charge balance.

The degree of alkoxylation, mole ratio of ethylene oxide to propylene oxide, the hydrophobic nature of the "R1" group, and the counter ion of the sulfate, taken together result in maximum efficiency and flexibility of properties as surface active agents.

The compounds of this invention can be tailored to specific applications by the selecting the proper "R" groups, the degree of alkoxylation in both locations of the molecule ($R^2$ and $R^3$), and the relative amounts of ethylene oxide and propylene oxide present in the molecule.

The preparation of the alkoxylated ether amines are known to those skilled in the art and are items of commerce marketed by Tomah Products. The technology is summarized by the following equation cyanoethylation-hydrogenation reaction sequence;

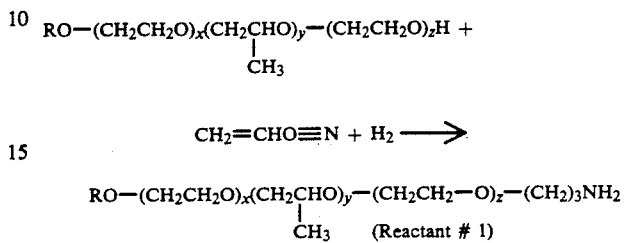

One specific group of ether amines, commercially available from Tomah Products, useful in the preparation of the compounds of this invention are alkoxylated Guerbet Alcohols. These regiospecific beta branched alcohols have been known since the 1890's when Marcel Guerbet first synthesized them. (M. Guerbet, C. R. Acad. Sci. Paris, 128, 511; 1002 (1899)). These materials are high in molecular weight and are liquid to very low temperatures. The guerbet reaction gives very specific branching in the alcohol as shown;

As can be seen by the above reaction the molecules have substitution on the second carbon from the hydroxyl group. This branching has been found to be critical to the preparation of a product having the desired properties. If the branching were on the same carbon as the hydroxyl group, the hydroxyl group would be a secondary one and would be very hindered and has low reactivity. As one moves the branch position away from the beta carbon, the liquidity, and substantivity to hair and fiber decreases.

Guerbet alcohols that are the reaction product of one specific raw material alcohol will result in a so called "homo-guerbet". In this case R' and R" are identical. If the starting alcohols used in the guerbet reaction are of differing molecular weights a so called "hetero-guerbet" results. This type of guerbet has a mixed distribution of all possible combinations of alcohols. For this reason R and R' in the generic formula may be the same or different.

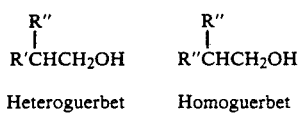

Heteroguerbet    Homoguerbet

The use of guerbet derived ether amines to prepare compounds of this invention can result in highly substantive liquid products. The high molecular weight of the hydrophobe allows for better oil solubilization using these surfactants over conventional surfactants.

EXAMPLES

Preparation of the Amido Alcohol

Reaction Sequence

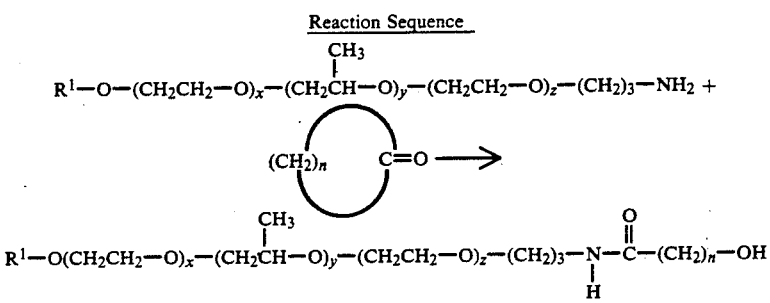

EXAMPLE A-W

Example A

Introduce into a suitable flask, equipped with agitation, nitrogen sparge and heating ability, 86.0 grams of butyrolactone and the specified number 324.0 grams of Reactant A. The contents of the flask are then heated to between 50 and 75 C. and held for three to eight hours. The reaction is complete, when the free amine measured by alkali value becomes very low.

Example B-W

Example A is repeated, only substituting the number of grams and type of amine specified in the following table.

| Example | R | x | y | z | Grams |
|---|---|---|---|---|---|
| A | C10H21 | 0 | 4 | 2 | 324.0 |
| B | C18H38 | 2 | 2 | 2 | 622.0 |
| C | C20H42 | 0 | 0 | 6 | 620.0 |
| D | C16H34 | 0 | 6 | 0 | 654.0 |
| E | C18=H36 | 0 | 6 | 4 | 856.0 |
| F | C10H21 | 3 | 6 | 3 | 833.0 |
| G | C18H34 | 0 | 3 | 0 | 501.0 |
| H | C18H34 | 0 | 0 | 0 | 237.0 |
| I | C18H34 | 1 | 1 | 1 | 501.0 |

Preparation of a Guerbet Alkoxylated Ether Amine Based Amino Alcohol $R^1$ is:

$$R'CHCH_2-\overset{R''}{|}$$

| Example | R' | R'' | x | y | z | Grams |
|---|---|---|---|---|---|---|
| J | C8 | C10 | 0 | 0 | 0 | 355.0 |
| K | C8 | C10 | 1 | 1 | 1 | 502.0 |
| L | C8 | C10 | 0 | 5 | 2 | 399.0 |
| M | C8 | C10 | 5 | 5 | 5 | 1092.0 |
| N | C8 | C10 | 10 | 10 | 10 | 1825.0 |
| O | C11 | C13 | 0 | 0 | 0 | 379.0 |
| P | C11 | C13 | 1 | 1 | 1 | 584.0 |
| Q | C11 | C13 | 0 | 5 | 2 | 399.0 |
| R | C11 | C13 | 5 | 5 | 5 | 1172.0 |
| S | C11 | C13 | 10 | 10 | 10 | 1907.0 |
| T | C16 | C18 | 0 | 0 | 0 | 506.0 |
| U | C16 | C18 | 1 | 1 | 1 | 653.0 |
| V | C16 | C18 | 0 | 5 | 2 | 889.0 |
| W | C16 | C18 | 5 | 5 | 5 | 1241.0 |
| X | C16 | C18 | 10 | 10 | 10 | 1976.0 |

SULFATION OF THE AMIDO ALCOHOL

Examples 1–7 Procedure (Chlorosulfonic Acid)

Example 1

To 410.0 grams of reaction product example A, is slowly added 117.0 grams of chlorosulfonic acid, under a slight vacuum. The addition is very exothermic and rate of addition is regulated by cooling rate (i.e. keeping the temperature below 30 C.) and removal of HCl generated as a by-product. After all the chlorosulfonic acid has been added increase the vacuum until all bubbling ceases. Release vacuum.

Prepare a neutralization solution by mixing 40.0 grams of sodium hydroxide in 1,000 grams of water. Slowly add the chlorosulfonic acid/alcohol adduct to the neutralization solution under good agitation. After all the adduct is added, adjust the pH to 7.0 with either sodium hydroxide or citric acid. The product is an aqueous solution of the products of this invention and is used without and additional purification.

Example 2–4

Repeat example 1 except substitute the indicated amount of reaction products from reactions B–D for reaction product example A.

Example 5–7

Repeat example 1 except substitute the indicated amount of reaction products from examples E–G for reaction product example A and 56.1 grams of KOH for the 40.0 grams of NaOH.

| Example | Product of Example | R | x | y | z | Grams |
|---|---|---|---|---|---|---|
| 1 | A | C10H21 | 0 | 4 | 2 | 410.0 |
| 2 | B | C18H38 | 2 | 2 | 2 | 708.0 |
| 3 | C | C20H42 | 0 | 0 | 6 | 706.0 |
| 4 | D | C16H34 | 0 | 6 | 0 | 740.0 |
| 5 | E | C18=H36 | 0 | 6 | 4 | 942.0 |
| 6 | F | C10H21 | 3 | 6 | 3 | 919.0 |
| 7 | G | C18H34 | 0 | 3 | 0 | 587.0 |
| 8 | H | C18H34 | 0 | 0 | 0 | 323.0 |
| 9 | I | C18H34 | 1 | 1 | 1 | 587.0 |

Examples 8–18 Procedure (Sulfamic Acid)

Example 8

To a suitable vessel is added 102.0 add grams of sulfamic acid, and 0.1 grams of urea and 323.0 grams of the reaction product example H under good agitation. Heat to 100 to 120 C. under nitrogen sparge. After this period the reaction is followed by anionic actives which will reach 97+$°/_{oo}$ Add 1,000 grams of a 1% NaOH solution, after cooling to below 85 C. The product is an aqueous solution of the desired sulfate, and is used without any additional purification.

Example 9-18

Repeat example 8 except substitute the indicated amount of reaction products examples H-R for reaction product example H.

| Example | Product of Example | R' | R" | x | y | z | Grams |
|---|---|---|---|---|---|---|---|
| 10 | J | C8 | C10 | 0 | 0 | 0 | 441.0 |
| 11 | K | C8 | C10 | 1 | 1 | 1 | 588.0 |
| 12 | L | C8 | C10 | 0 | 5 | 2 | 485.0 |
| 13 | M | C8 | C10 | 5 | 5 | 5 | 1178.0 |
| 14 | N | C8 | C10 | 10 | 10 | 10 | 1911.0 |
| 15 | O | C11 | C13 | 0 | 0 | 0 | 465.0 |
| 16 | P | C11 | C13 | 1 | 1 | 1 | 670.0 |
| 17 | Q | C11 | C13 | 0 | 5 | 2 | 485.0 |
| 18 | R | C11 | C13 | 5 | 5 | 5 | 1258.0 |

Examples 19-24 Procedure (Chlorosulfonic Acid)

Example 19-21

Repeat example 1 except substitute the indicated amount of reaction product from examples S-U for reaction product example A.

Example 22-24

Repeat example 1 except substitute the indicated amount of reaction products from examples U-X for reaction product from example A and 56.1 grams of KOH for the 40.0 grams of NaOH.

| Example | Product of Example | R' | R" | x | y | z | Grams |
|---|---|---|---|---|---|---|---|
| 19 | S | C11 | C13 | 10 | 10 | 10 | 1993.0 |
| 20 | T | C16 | C18 | 0 | 0 | 0 | 592.0 |
| 21 | U | C16 | C18 | 1 | 1 | 1 | 739.0 |
| 22 | V | C16 | C18 | 0 | 5 | 2 | 975.0 |
| 23 | W | C16 | C18 | 5 | 5 | 5 | 1327.0 |
| 24 | X | C16 | C18 | 10 | 10 | 10 | 2062.0 |

APPLICATIONS EXAMPLES

Hydrolysis of Sulfated Amide

To our surprise, the compounds of this invention show outstanding hydrolytic stability compared to the amidosulfates known previously.

| Prior Art Compounds | Half life time in minutes for concentration to reduce by 50%. |
|---|---|
| Amido sulfates | |
| C11H23—C(O)NHCH2CH2OSO3 Na | 85 |
| C15H31—C(O)NHCH2CH2OSO3 Na | 80 |
| C17H35—C(O)NHCH2CH2OSO3 Na | 82 |
| C17H35—C(O)NCH3—CH2CH2OSO3 Na | 9 |
| C11H23—C(O)NHCH2CH2(EO)3—OSO3 Na | 96 |
| C15H31—C(O)NHCH2CH2—(EO)3—OSO3 Na | 107 |
| C17H35—C(O)NHCH2CH2—(EO)3—OSO3 Na | 98 |
| Compounds of this invention | |
| Example #7 | 300 |
| Example #9 | 405 |
| Example #14 | 400 |
| Example #18 | 496 |

Wet Comb Out Test

A laboratory test is conducted to screen the wet comb properties of a representative member of the family of novel compounds. Hair swatches are purchased from a supply of human hair from the same head. Each test swatch contains 7 grams of hair and is 11 inches in length. The hair is tied tightly 1 inch from one end with string. The swatch is pre-cleaned with a 3% solution of ammonium lauryl sulfate. Subsequently, the swatch is washed under running tap water. The hair is then squeezed out and while still damp dipped into a 200 ml solution of 0.2% active quaternary. Another rinse is made, then the swatch is blotted dry. The swatch is then treated by holding the hair swatch, combing the hair as rapidly as possible while alternating the side of the swatch combed. The time needed to get one smooth free stroke without tangling is recorded. Typical results for the standard quaternary compounds used in hair conditioning (stearyldimethylbenzyl ammonium chloride) range from 12-14 seconds.

| Rinse Conditioner (Wet Comb Out Test) | |
|---|---|
| Product | Time in Seconds |
| Product Example #7 | 12 |
| Product Example #14 | 14 |
| Stearyldimethylbenzyl ammonium chloride | 12 |

As can be seen, the compounds of the invention give significant conditioning properties to hair, and coupled with their mild nature with regard to skin and eyes, makes it a prime candidate for cosmetic applications.

What is claimed is:

1. A sulfated amido compound which conforms to the following formula:

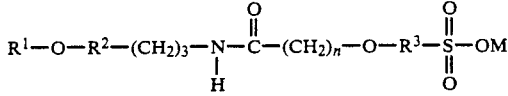

$R^1$ is alkyl having from 6 to 40 carbon atoms;
$R^2$ is —(CH$_2$—CH$_2$—O)$_x$—(CH$_2$—CH—(CH$_3$)—O)$_y$—(CH$_2$—CH$_2$—O)$_z$—;
$R^3$ is —(CH$_2$—CH$_2$—O)$_a$—(CH$_2$—CH—(CH$_3$)—O)$_b$—(CH$_2$—CH$_2$—O)$_c$—;
n is an integer from 1 to 10;
x, y and z are independently integers from 0 to 20;
a, b and c are independently integers from 0 to 20;
M is an selected from Na, K, Li, Ba, Mg, Ca, and NH$_4$, and is needed for charge balance.

2. A compound of claim 1 wherein a, b and c are 0.

3. A compound of claim 1 wherein x, y and z are 0.

4. A compound of claim 1 wherein $R^1$ conforms to the following structure;

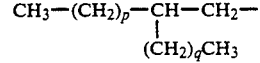

p and q are integers from 2 to 17.

5. A compound of claim 4 wherein p is 5 and q is 7.

6. A compound of claim 1 wherein x is 3, y is 5 and z is 10.

7. A compound of claim 1 wherein a is 5, b is 1, and c is 9.

8. A compound of claim 1 wherein $R^1$ is alkyl having 10 to 20 carbon atoms.

9. A compound of claim 1 wherein $R^1$ is alkyl having 12 to 18 carbon atoms.

10. A compound of claim 1 wherein $R^1$ is alkyl having 12 carbon atoms.

11. A compound of claim 1 wherein $R^1$ is alkyl having 14 carbon atoms.

12. A compound of claim 1 wherein n is 3.

13. A compound of claim 1 wherein n is 2.

* * * * *